United States Patent [19]

Künstle et al.

[11] Patent Number: 4,571,433

[45] Date of Patent: Feb. 18, 1986

[54] PROCESS FOR STABILIZING AQUEOUS SOLUTIONS OF ACETOACETAMIDES WITH SIMULTANEOUS REDUCTION IN THE CONTENT OF β-AMINOCROTONIC ACID AMIDES

[75] Inventors: Gerhard Künstle; Herbert Jung, both of Burghausen, Fed. Rep. of Germany

[73] Assignee: Wacker-Chemie GmbH, Munich, Fed. Rep. of Germany

[21] Appl. No.: 648,969

[22] Filed: Sep. 10, 1984

[30] Foreign Application Priority Data

Sep. 29, 1983 [DE] Fed. Rep. of Germany ....... 3335425

[51] Int. Cl.$^4$ ................ C07C 102/00; C07C 103/147
[52] U.S. Cl. ....................................................... 564/4
[58] Field of Search ........................................... 564/4

[56] References Cited

U.S. PATENT DOCUMENTS 2,863,918  12/1958  Bikales et al. ........................ 564/4

Primary Examiner—Paul F. Shaver
Attorney, Agent, or Firm—Collard, Roe & Galgano

[57] ABSTRACT

A process for stabilizing aqueous solutions of acetoacetamides which simultaneously results in the reduction of β-aminocrotonic acid amide content. According to the process, to aqueous acetoacetamide solutions which have been prepared in a known manner by the reaction of diketene with ammonia or water-soluble primary or secondary aliphatic amines under basic conditions, sufficient amounts of diketene are added immediately after their preparation thereto at room temperature with vigorous stirring, to maintain a pH value of 6–7. The so obtained aqueous solutions of the acetoacetamides are not only substantially stable, but also especially pure since these solutions are neither contaminated by salt-like by-products nor by derivatives of β-aminocrotonic acid amides.

2 Claims, No Drawings

PROCESS FOR STABILIZING AQUEOUS SOLUTIONS OF ACETOACETAMIDES WITH SIMULTANEOUS REDUCTION IN THE CONTENT OF β-AMINOCROTONIC ACID AMIDES

The present invention relates to a process for stabilizing aqueous solutions of acetoacetamides while simultaneously affording a reduction in the content of β-aminocrotonic acid amides.

Acetoacetamides, especially acetoacetamide, N-monoalkyl- and N,N-dialkylacetoacetamides, whose alkyl radicals contain 1–6 C-atoms, are used as intermediates in the preparation of pharmaceuticals, plant protecting agents and dyestuffs. For easier handling, they are preferably used in the form of aqueous solutions.

It is known to produce aqueous solutions of acetoacetamides by the reaction of diketene with excess ammonia or water-soluble, aliphatic primary or secondary amines in water (compare "Methoden der organishen Chemie" by Houben-Weyl, Vol. 7/4, 4th edition 1968, pp. 233–236 and U.S. Pat. No. 2,152,1 32).

It is also known to prepare concentrated aqueous solutions of acetoacetamides by the reaction of diketene with salts of weak acids and ammonia, e.g., ammonium carbonate or bicarbonate, or salts of a carboxylic acid and primary aliphatic amines in an approximately stoichiometric ratio in an aqueous medium (compare CH-PS 287 558 and U.S. Pat. No. 2,615,917). Since $CO_2$-development occurs during the reaction, these processes cannot be carried out continuously with constant control of the pH value on which the formation of by-products depends. That is the reason why, especially in the preparation of concentrated aqueous acetoacetamide solutions by reaction with diketene, an excess amount of ammonia is used, in order to maintain a pH value of 9.5–10. (Compare DE-AS 1,125,418 which corresponds to G.B. Pat. No. 828,423). Similarly, the concentration of diluted aqueous acetoacetamide solutions is carried out in the presence of an excess of ammonia, to which obviously a prevention of decomposition of the acetoacetamide or a stabilizing effect on the same in aqueous solution is attributed. (See G.B. Pat. No. 832,956).

It is, therefore, known that aqueous acetoacetamide solutions in the presence of excessive ammonia, or amine respectively, can be produced with greater selectivity as regards the acetoacetamide content than under practically neutral conditions, when more by-products will be formed. But it is also known that such aqueous acetoacetamide solutions, which from their preparation exhibit a pH value higher than 9, have only a limited stability, i.e., the content of the originally present acetoacetamide will clearly decrease, because the acetoacetamides tend to decompose and/or form by-products by further reaction, a fact which cannot be adequately compensated by the assumed stabilization by ammonia.

According to a known process for the stabilization of such acetoacetamides prepared under basic conditions, the aqueous solutions are, after the reaction is completed, adjusted to a pH value of 6–7.5 by the addition of an acid. (See DE 31 08 622 Al). The storage stability of the aqueous acetoacetamide solutions is, in that case, dependent on the type of the acetoacetamides, as well as on the concentration, i.e., the content of acetoacetamide, and the storage temperature. The stability increases in the following order (least stable to most stable): unsubstituted acetoacetamide, monalkylsubstituted acetoacetamide, and dialkylsubstituted acetoacetamide.

At room temperature the aqueous solutions stabilized by acid addition, having a slightly acid to neutral reaction, practically do not show any decrease of the original acetoacetamide content upon standing for a prolonged time. However, with the addition of an acid, salt-like by-products are formed, which practically cannot be removed, whereby the purity of the aqueous acetoacetamide solutions is impaired. Moreover, the β-aminocrotonic acid amide derivatives, which, as known, are already formed when acetoacetamide is produced under basic conditions, and are therefore visibly present in the aqueous solutions, remain entirely unaffected by the added acid. As a result, they are capable of further reaction in the slightly acid or neutral medium, in a known manner, thereby forming nicotinic acid derivatives, which also impair the purity of the aqueous acetoacetamide solutions.

It is therefore the object of the present invention to provide a process for the stabilization of aqueous solutions of acetoacetamides with, simultaneously, a decrease in the β-aminocrotonic acid amides content by improving the known reaction of diketene with excessive amounts of ammonia or water-soluble aliphatic primary or secondary amines in aqueous solution while maintaining a pH value of 8–10.

It is a more particular object of the present invention to provide such an improved process which not only counteracts the tendency of the acetoacetamides to decompose and/or form by-products by further reaction, but also maintains the purity of the stabilized solutions by keeping them free of salt-like by-products and of derivatives of β-aminocrotonic acid amides and other derivatives formed therefrom.

This is accomplished according to the invention by adding to the aqueous solutions of the acetoacetamides, immediately after their preparation, a sufficient amount of diketene at room temperature and with vigorous agitation so as to ensure maintenance of a pH value of 6 to 7.

It is of decisive importance to maintain the pH value at 6 to 7, because the intended stabilization with simultaneous reduction of the content in β-aminocrotonic acid amide derivatives cannot be warranted at pH values below 6 and above 7. Preferably, the amount of diketene is so chosen that a pH value of 6.5 will be maintained in the aqueous solution. Those amounts of diketene depend, on the one hand, on the pH value at the start and, on the other hand, on the content of β-aminocrotonic acid amide derivatives present in the aqueous acetoacetamide solutions immediately after their preparation.

The aqueous acetoacetamide solutions prepared by means of the addition of diketene according to the invention with a preferably slightly acid reaction corresponding to a pH value of 6.5, are very stable, i.e., after standing for 60 days at room temperature they practically do not show any decrease in the acetoacetamide content and, at higher temperatures of about 50° C., they clearly show a lower reduction of the acetoacetamide content than unstabilized solutions. Moreover, the diketene treatment surprisingly simultaneously reduces the content of the originally present β-aminocrotonic acid amide derivatives, because under the given conditions they react with diketene to effect re-formation of the corresponding acetoacetamides and are no longer available for further reaction to form nicotinic acid derivatives.

The acetoacetamide solutions made according to the invention are not only sufficiently stable, but also especially pure, since the stabilized solutions are neither contaminated by salt-like by-products, the formation of which cannot be prevented in the stabilization by the simple addition of an acid, nor by further reaction products of β-aminocrotonic acid amide derivatives. Consequently, the stabilized aqueous solutions can be processed directly and also after prolonged standing, without further operations being necessary for the isolation of the acetoacetamides themselves, or for the purification of the aqueous solutions.

In the following, the invention will be illustrated by a number of examples. In these examples, the acetoacetamides were always prepared in a known manner by reaction of diketene with excessive amounts of ammonia or monoalkyl- or dialkylamines in aqueous solution. Then the pH value, as well as the content of acetoacetamide and β-aminocrotonic acid amide, were determined immediately after the preparation and after the treatment with diketene at the beginning and after the indicated time of standing at the indicated temperature.

EXAMPLE 1

A freshly prepared approximately 70% by weight aqueous solution of N-methyl-acetoacetamide with a pH value of 8.0 was divided into parts and one part was adjusted with pure diketene to a pH value of 6.5 while being mixed well at room temperature ( =stabilized specimen). After standing for a time ranging from 0, 30, to 60 days at 50° C., the stabilized and the unstabilized specimens were analyzed. The results are shown in Table 1.

TABLE 1

| Standing Time In Days | pH value Stab. | pH value Not Stab. | of N—methyl-acetoacetamide Stab. | of N—methyl-acetoacetamide Not Stab. | of N—methylamino-crotonic acid-N—methylamide Stab. | of N—methylamino-crotonic acid-N—methylamide Not Stab. |
|---|---|---|---|---|---|---|
| 0 | 6.5 | 7.5 | 73.0 | 72.9 | <<0.01 | 0.13 |
| 30 | 6.4 | 7.2 | 72.8 | 70.25 | <<0.01 | 0.09 |
| 60 | 6.4 | 7.0 | 72.6 | 69.4 | <<0.01 | 0.06 |

By means of the diketene, the N-methylaminocrotonic acid-N-methylamide was practically completely converted into N-methyl-acetoacetamide. The relative decrease of the content in N-methyl-acetoacetamide after 60 days was 0.5% in the stabilized specimen, and 4.8% in the nonstabilized comparison specimen.

EXAMPLE 2

A 31% by weight aqueous solution of acetoacetamide with a pH value of 9.0 was divided into parts and one part was adjusted to a pH value of 6.5 with pure diketene while being mixed well at room temperature ( =stabilized specimen). After a standing time of 0, 30, and 60 days at 30° C., the stabilized and unstabilized specimens were analyzed. The results are shown in Table 2.

TABLE 2

| Standing Time In Days | pH value Not Stab. | pH value Stab. | acetoacetamide Not Stab. | acetoacetamide Stab. | aminocrotonic acid amide Not Stab. | aminocrotonic acid amide Stab. |
|---|---|---|---|---|---|---|
| 0 | 9.0 | 6.5 | 31.2 | 33.4 | 2.3 | Traces |
| 30 | 8.3 | 7.0 | 25.9 | 32.1 | 1.6 | Traces |
| 60 | 7.7 | 7.0 | 23.7 | 31.3 | 0.4 | Traces |

The aminocrotonic acid amide was practically completely converted into acetoacetamide by the diketene. At the same time, a clearly observable stabilizing effect was accomplished: the decrease of the acetoacetamide content in the stabilized specimen after 60 days amounted to 6.3%, whereas the decrease was 24% in the unstabilized comparison specimen.

EXAMPLE 3

Prepared were 70% by weight aqueous solutions of

| | N—methyl-acetoacetamide | (specimen A) |
| | N,N—dimethyl-acetoacetamide | (specimen B) |
| and | N,N—diisopropyl-acetoacetamide | (specimen C) | with different pH values, and immediately after their preparation, they were divided into parts and one part of each was adjusted to a pH value of 6.5 by adding pure diketene while mixing well at room temperature. After a standing time of 0, 30, and 60 days at 50° C., the solutions were analyzed.

The results are listed in Table 3.

TABLE 3

Specimen A

Content in % by weight of

| Standing Time in days | pH-value Stab. | pH-value Not Stab. | N—methylaceto-acetamide Stab. | N—methylaceto-acetamide Not Stab. | N—methylamino-crotonic acid N—methylamide Stab. | N—methylamino-crotonic acid N—methylamide Not Stab. |
|---|---|---|---|---|---|---|
| 0 | 6.5 | 7.2 | 70.0 | 70.0 | <<0.01 | 0.06 |
| 30 | 6.4 | 7.1 | 70.0 | 69.4 | <<0.01 | 0.05 |
| 60 | 6.3 | 7.1 | 70.0 | 69.3 | <<0.01 | 0.03 |

Specimen B

Content in % by weight of

| Standing Time in days | pH-value Stab. | pH-value Not Stab. | N,N—dimethyl-acetoacetamide Stab. | N,N—dimethyl-acetoacetamide Not Stab. | N,N—dimethyl-crotonic acid N,N—dimethylamide Stab. | N,N—dimethyl-crotonic acid N,N—dimethylamide Not Stab. |
|---|---|---|---|---|---|---|
| 0 | 6.5 | 7.0 | 70.0 | 70.0 | <<0.01 | <0.01 |
| 30 | 6.5 | 7.0 | 70.0 | 70.0 | <<0.01 | <0.01 |
| 60 | 6.4 | 7.0 | 70.0 | 69.9 | <<0.01 | <0.01 |

Specimen C

Content in % by weight of

| Standing Time in days | pH-value Stab. | pH-value Not Stab. | N,N—diisopropyl-acetoacetamide Stab. | N,N—diisopropyl-acetoacetamide Not Stab. | N,N—diisopropyl-aminocrotonic acid-N,N—diiso-propyl amide Stab. | N,N—diisopropyl-aminocrotonic acid-N,N—diiso-propyl amide Not Stab. |
|---|---|---|---|---|---|---|
| 0 | 6.5 | 7.3 | 70.0 | 70.0 | <<0.01 | <0.01 |
| 30 | 6.5 | 7.2 | 70.0 | 69.5 | <<0.01 | <0.01 |
| 60 | 6.3 | 7.2 | 70.0 | 69.3 | <<0.01 | <0.01 |

Specimen A, N-methyl-acetoacetamide, results from a more pure starting solution compared with those of Example 1. The stabilization effect with diketene is therefore lower in comparison with Example 1 but still significantly detectable (cf. no decrease in the content in N-methyl-acetoacetamide after 60 days and practically no content in N-methylaminocrotonic acid-N-methylamide). Specimen B and C are the two dialkyl-substituted acetoacetamides which, per se, are more stable than monoalkyl-substitued and unsubstituted acetoacetamides, respectively, as disclosed in the specification on page 3, lines 1 to 4. The stabilization effect with diketene is therefore low but still significantly detectable.

While only several embodiments and examples of the present invention have been described, it is obvious that many changes and modifications may be made thereunto, without departing from the spirit and scope of the invention.

What is claimed is:

1. In an improved process for stabilizing aqueous solutions of acetoacetamides and simultaneously reducing the content of β-aminocrotonic acid amides of the type including the step of reacting diketene with excess ammonia or primary or secondary amines in aqueous solutions while maintaining a pH value of 8–10, the improvement comprising the step of:

adding to the aqueous solutions of the acetoacetamides immediately after their preparation a sufficient amount of diketene at room temperature with vigorous agitation to obtain a pH value of 6–7.

2. The process of claim 1, wherein said diketene is added in an amount sufficient to maintain a pH value of 6.5 in the aqueous solution.

* * * * *